United States Patent [19]

Pazzaglia et al.

[11] Patent Number: 5,245,856
[45] Date of Patent: Sep. 21, 1993

[54] PORTABLE TESTING DEVICE FOR MEASURING STATIC AND DYNAMIC DRAG FRACTORS

[76] Inventors: Randy Pazzaglia, P.O. Box 1853, Bryan, Tex. 77806; Gary S. Nelson, 1005 Sonoma Ct., College Station, Tex. 77840

[21] Appl. No.: 819,768

[22] Filed: Jan. 13, 1992

[51] Int. Cl.[5] .............................................. G01N 19/02
[52] U.S. Cl. ............................................................ 73/9
[58] Field of Search ........................................ 73/9, 10

[56] References Cited

U.S. PATENT DOCUMENTS

| | | | |
|---|---|---|---|
| 2,225,140 | 12/1940 | Walker | 73/9 |
| 2,531,906 | 11/1950 | Christian | 73/9 |
| 3,893,330 | 7/1975 | Shute et al. | 73/9 |
| 4,187,714 | 2/1980 | Cox et al. | 73/9 |
| 4,212,063 | 7/1986 | Hardmark | 73/9 |
| 4,594,878 | 6/1986 | Abe et al. | 73/9 |
| 4,779,447 | 10/1988 | Rath | 73/9 |
| 4,813,266 | 3/1989 | Nash | 73/9 |
| 4,895,015 | 1/1990 | English | 73/9 |

OTHER PUBLICATIONS

Irvine, Horizontal Pull Slipmeter, ASTM Method F:609-79, Mar. 1989.

*Primary Examiner*—Robert Raevis

[57] ABSTRACT

A portable testing device designed to provide slope compensated static and dynamic drag factors. A test material is mounted on a dragging block which is then placed on the test surface. A cable is attached to the dragging block, passed through a foot held pulley device and attached to a rod which protrudes out of an electronics box. The user pulls on the cable while holding onto handgrips attached to the electronics box. This causes the dragging block to be pulled across the test surface. The strain caused by the forces created by the friction between the test surface and the test material is measured using a strain gauge. This strain is used, along with the weight of the dragging block, to determine the slope compensated drag factors.

12 Claims, 8 Drawing Sheets

PORTABLE TESTING DEVICE FOR MEASURING STATIC AND DYNAMIC DRAG FRACTORS

BACKGROUND

1. Field of Invention

The present invention relates to a method and apparatus for determining the drag factor that exists when two surfaces are in contact and move relative to each other.

2. Description of Prior Art

When gravity supplies the normal force, the term "drag factor" is synonymous with the coefficient of friction if the two surfaces are horizontal. The drag factor will differ from the coefficient of friction when measured on inclines as the drag factor alone measures the combined influence of the coefficient of friction and the slope of the incline. By measuring on an incline, the results will reflect the effect of the incline in overcoming the friction forces between the two surfaces. This could be important in accident reconstruction because it will provide a direct measure of the actual drag factor at work, a slope compensated static or dynamic drag factor. Currently, it is common in accident reconstruction for a coefficient of friction to be used in conjunction with a correction grade drag factor in order to estimate the drag factor.

There are several known methods to measure the coefficient of friction or the drag factor. A widely used device for the measurement of the drag factor is the Horizontal Pull Slipmeter, hereinafter referred to by the acronym HPS. The HPS was developed by C. H. Irvihe of Liberty Mutual Insurance Company of Hopkinton, Mass. It is described in ASTM Method F:609-79. The HPS consists of two basic elements, a drag sled mounted on slider feet and equipped with a force gauge and a means for pulling the sled at a controlled rate of speed across the surface being tested. A drawback to this device is that the alignment of the pulling mechanism is not controlled. This may introduce an additional variable which could affect measurement accuracy. In addition, this type of device is susceptible to drag sled bounce or hop. Drag sled hop occurs when the frictional force between the drag sled and the test surface is abruptly overcome by the increasing pulling force on the drag sled. Depending on test conditions, the drag sled hop can increase in a nonrecoverable manner rendering the test results invalid. In addition, a separate drag sled is required for each different material to be tested. Thus, this type of device does not allow for easy testing of different materials. Another device, U.S. Pat. No. 4,895,015 issued to English in January 1990, is an improvement to the horizontal pull slipmeter which utilizes a drag sled and a stationary pulling mechanism with a set of guide tracks. The drag sled is pulled by a motor and guided along the tracks which assure the alignment of the pull. The force required to pull the drag sled is measured thus allowing the determination of the drag factor. However, the guide rails may introduce some error if they are not correctly aligned which may cause the drag sled to bind and thus affect the accuracy of the test. Also, if the surface is not perfectly flat the sled will bind on the rails introducing an error. In addition, the friction of the drag sled with the rails will effect the test results by inflating the force needed to pull the drag sled and thus inflating the measured drag factor.

Another device, U.S. Pat. No. 4,813,266 issued to Nash in March 1989, consists of a test block connected to a microprocessor. The bottom of the test block is covered with the material whose drag factor is desired. The test block is set on the test surface and the block is given an impulse with a hammer or other object. The impulse causes the block to move along the surface. An accelerometer on the test block transmits acceleration data to the microprocessor. The acceleration data includes information on the acceleration of the block caused by the impulse and the deceleration of the block as it comes to a stop after the impulse. This acceleration data is used by the microprocessor to determine the drag factor at a specific point on the test surface per measurement. This may be a drawback in some cases where it might be desirable to know the average value over some distance.

Three known devices utilize a motor vehicle to measure the drag factor between a tire and a road surface. These devices are:

1. U.S. Pat. No. 3,893,330 issued to Shute et al in July 1975 describes a device which utilizes a special fifth wheel on a vehicle to determine drag factor. While in motion the vehicles brakes are applied. The speed of the vehicle and the distance travelled before the vehicle stops after the brakes are applied are used to determine the drag coefficient;

2. U.S. Pat. No. 4,212,063 issued to Hardmark in July 1986 also uses a fifth wheel. The fifth wheel is mounted to a vehicle in such a manner that it can be lowered to come into contact with the road surface. The vertical forces acting on the measuring wheel are preset to known values. The torque acting on the fifth wheel is measured. This torsional force and the known vertical forces are used to determine the drag factor.

3. U.S. Pat. No. 4,779,447 issued to Rath in October 1988, delivers a different amount of brake pressure to one wheel of a vehicle than to another. When the vehicle is being driven and the brakes are applied the rotational speed of the wheels is compared to determine wheel slip. The wheel slip, brake torque and axle load are then used to determine the drag factor.

An inherent drawback with these devices is that in motor vehicle accident reconstruction the test vehicle must travel along the same path as the vehicle in the accident. In some cases this may be hazardous. For example, if an accident occurs at a sharp turn in the road or near a large dropoff, it may not be safe to drive the test vehicle along the same path as that taken by the vehicle involved in the accident. Also, in order to obtain an accurate reading the test vehicle must a similar breaking efficiency and tire rubber compound as the vehicle that was involved in the accident. This may be difficult to obtain in some cases. For example, if the vehicle involved in the accident was determined to have a leaking wheel cylinder, it would be difficult to duplicate this accurately on the test vehicle. Another drawback to these devices is that they are not easily portable. For example, if the accident reconstruction professional must travel a long distance to reach an accident site the test vehicle must be driven or otherwise transported to the site or the fifth wheel and other equipment must be transported to the site and installed on another vehicle at the accident site.

Another device, U.S. Pat. No. 4,594,878 issued to Abe et al in June 1986, uses a rotating tire which is lowered into contact with the surface to be measured.

The change in tire rotating speed is used to determine the drag factor. This differs from those devices that utilize a fifth wheel in that it is not mounted on a vehicle. Since the measuring apparatus is stationary it will not take into account the effect of an incline and thus will measure only the friction coefficient and will not provide a measure of the drag factor. In addition, this device will provide a measure of the coefficient of friction at only one point per measurement when in some cases it might be desirable to know the average value over some distance.

OBJECTS AND ADVANTAGES

Accordingly, several objects and advantages of this invention are:
(a) to provide a device that will measure static and dynamic drag factors and thus provide the user with a slope compensated drag factor;
(b) to provide a device that alerts the user if the pull test is improperly conducted;
(c) to provide a device that will allow for convenient and rapid testing of different materials;
(d) to provide a device that is easy to use;
(e) to provide a device that is easily portable;
(f) to provide a device that is relatively simple to manufacture and relatively inexpensive;
(g) to provide a device that resists friction test block "hop";

Further objects and advantages of this invention will become apparent from a consideration of the drawings and ensuing description of it.

REFERENCE NUMERALS IN DRAWINGS

| | |
|---|---|
| 34 | Test surface |
| 40 | Dragging device |
| 42 | Weight |
| 43 | Carrying handle |
| 45 | Butt plate |
| 46 | Free floating cushion pad |
| 48 | Replaceable friction pad |
| 50 A&B | Friction pad retention pin |
| 52 A&B | Cotter pin |
| 54 | Dragging attachment eyebolt |
| 56 | Pulling/measuring device |
| 58 | Pulling clip |
| 60 | Strain gauge rod |
| 62 | Electronics box |
| 64 | Key pad |
| 66 | Display |
| 68 | Handgrip |
| 70 | Foot held pulley device |
| 72 | Pulley |
| 74 A&B | Pulley support |
| 76 | Footrest |
| 77 | Dragging cable assembly |
| 78 | Dragging cable |
| 80 | Dragging cable clip |
| 81 | Dragging cable eye |
| 82 | Strain Gauge |
| 84 | Analog-to-digital convertor |
| 86 | Microprocessor |
| 88 | DC power supply |
| 90 | Angle measuring device |
| 92 | Rod |

DESCRIPTION OF INVENTION

Figure 1:
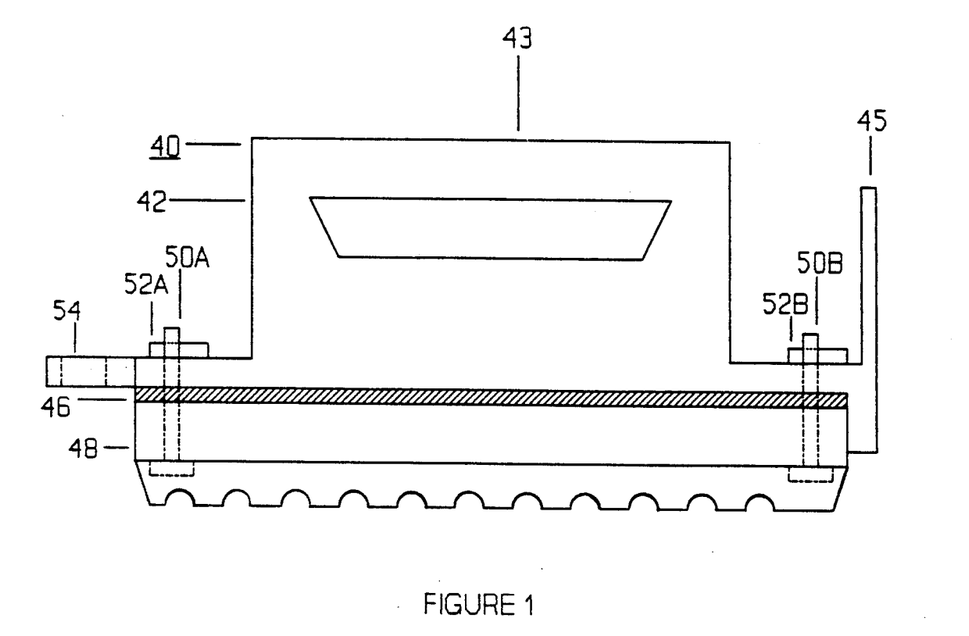
FIG. 1 provides a side view of the dragging device.
Figure 2:
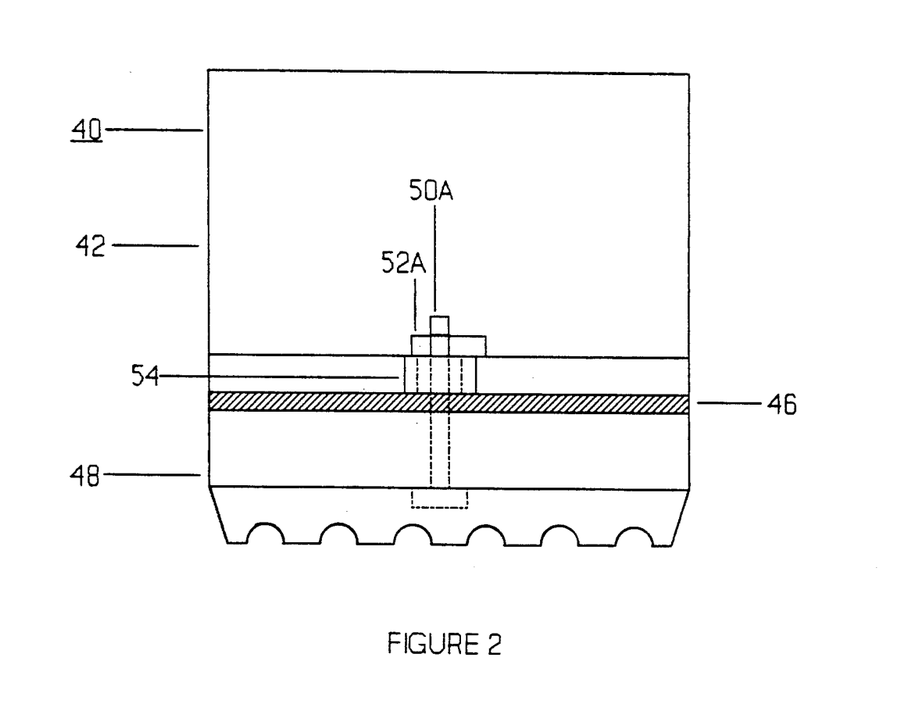
FIG. 2 provides a front view of the dragging device.

FIG. 1 provides a side view and FIG. 2 a front view of the dragging device 40. As shown in FIG. 1 and FIG. 2, a replaceable friction pad 48 forms the base of the dragging device 40. The replaceable friction pad 48 is made out of, or covered with, the material to be tested. The free floating cushion pad 46 is sandwiched between the replaceable friction pad 48 and the weight 42. The free floating cushion pad 46 is made out of a shock absorbing material and is not permanently affixed to either the replaceable friction pad 48 or the weight 42. The weight 42 is made out of a rigid material such as, but not limited to, steel or aluminum. The weight 42 rests on top of the free floating cushion pad 46. As can be seen in FIG. 1, the weight is formed with a butt plate 45 at one end. The butt plate 45 extends down and is in the edge of the replaceable friction pad 48 but does not extend all the way to the bottom of the replaceable friction pad 48. On the end of the weight 42 directly opposite the butt plate 45, a dragging attachment eyebolt 54 is attached to the weight 42. A carrying handle 43 is molded into the weight 42. The weight 42, free floating cushion pad 46, and the replaceable friction pad 48 are held together by two friction pad retention pins 50A and 50B, which pass through collinear holes in the weight 42, free floating cushion pad 46, and the replaceable friction pad 48. The heads of the friction pad retention pins 50A and 50B are recessed into the replaceable friction pad 48. The friction pad retention pins 50A and 50B are secured by cotter pins 52A and 52B which pass through holes in the friction pad retention pins 50A and 50B.

Figure 3:
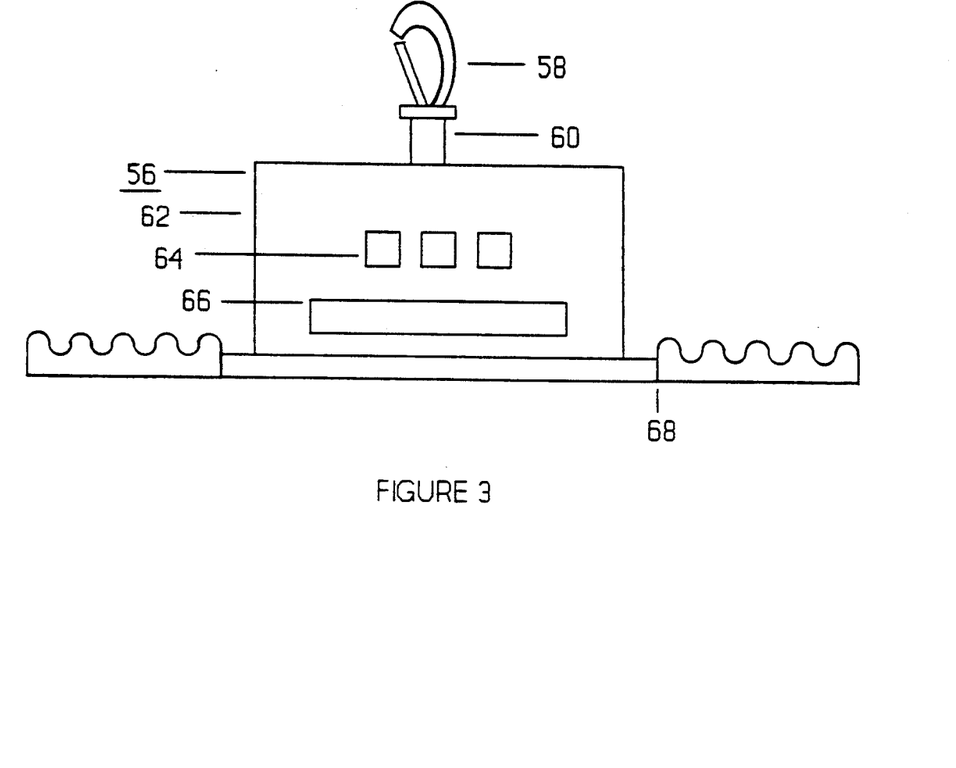
FIG. 3 provides a top view of the pulling/measuring device.
Figure 4:
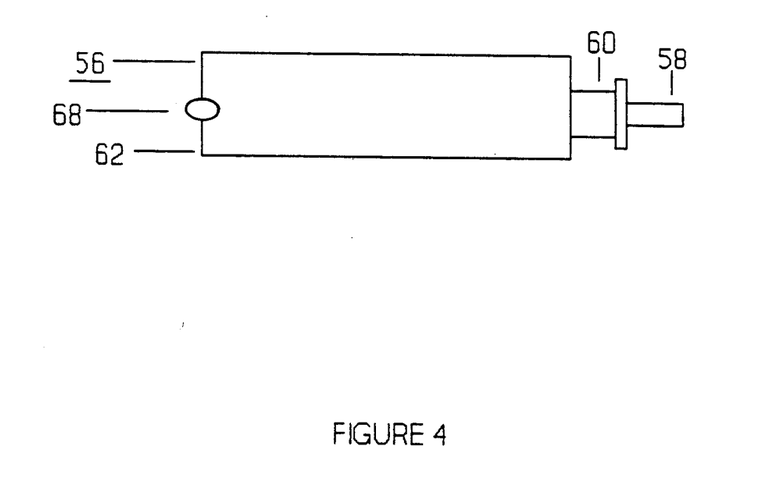
FIG. 4 provides a side view of the pulling/measuring device.

FIG. 3 shows a top view and FIG. 4 a side view of the pulling/measuring device 56. A handgrip 68 is firmly attached to electronics box 62. A key pad 64 and a display 66 are located on the electronics box 62. A strain gauge rod 60 extends out of the end of the electronics box 62 opposite the handgrip 68. The strain gauge rod 60 extends through the electronics box 62 and is firmly attached to the inside of the wall of the electronics box 62 that has the handgrip 68 attached on the outside. A pulling clip 58 is firmly attached to the end of the strain gauge rod 60 that extends out of electronics box 62.

Figure 5:
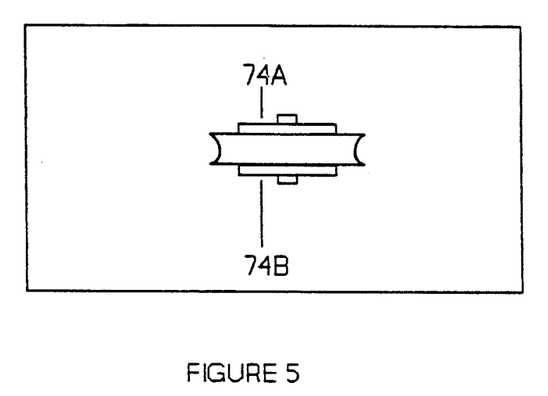
FIG. 5 provides a top view of the foot held pulley device.
Figure 6:
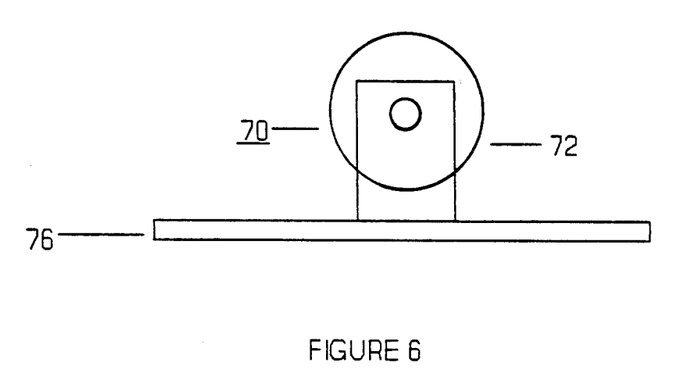
FIG. 6 provides a side view of the foot held pulley device.
Figure 7:
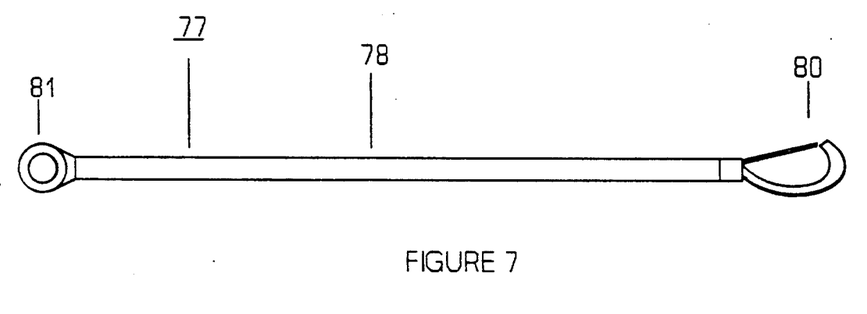
FIG. 7 shows the dragging cable with a clip at one end and an eye at the other end.

FIG. 5 shows a top view and FIG. 6 a side view of the foot held pulley device 70. The foot held pulley device 70 consists of a rigid footrest 76 to which the pulley supports 74A and 74B are firmly attached. The pulley 72 is supported and held in place by the pulley supports 74A and 74B. FIG. 7 shows the dragging cable assembly 77 with the dragging cable 78, dragging cable clip 80 on one end and the dragging cable eye 81 on the other.

Figure 8:
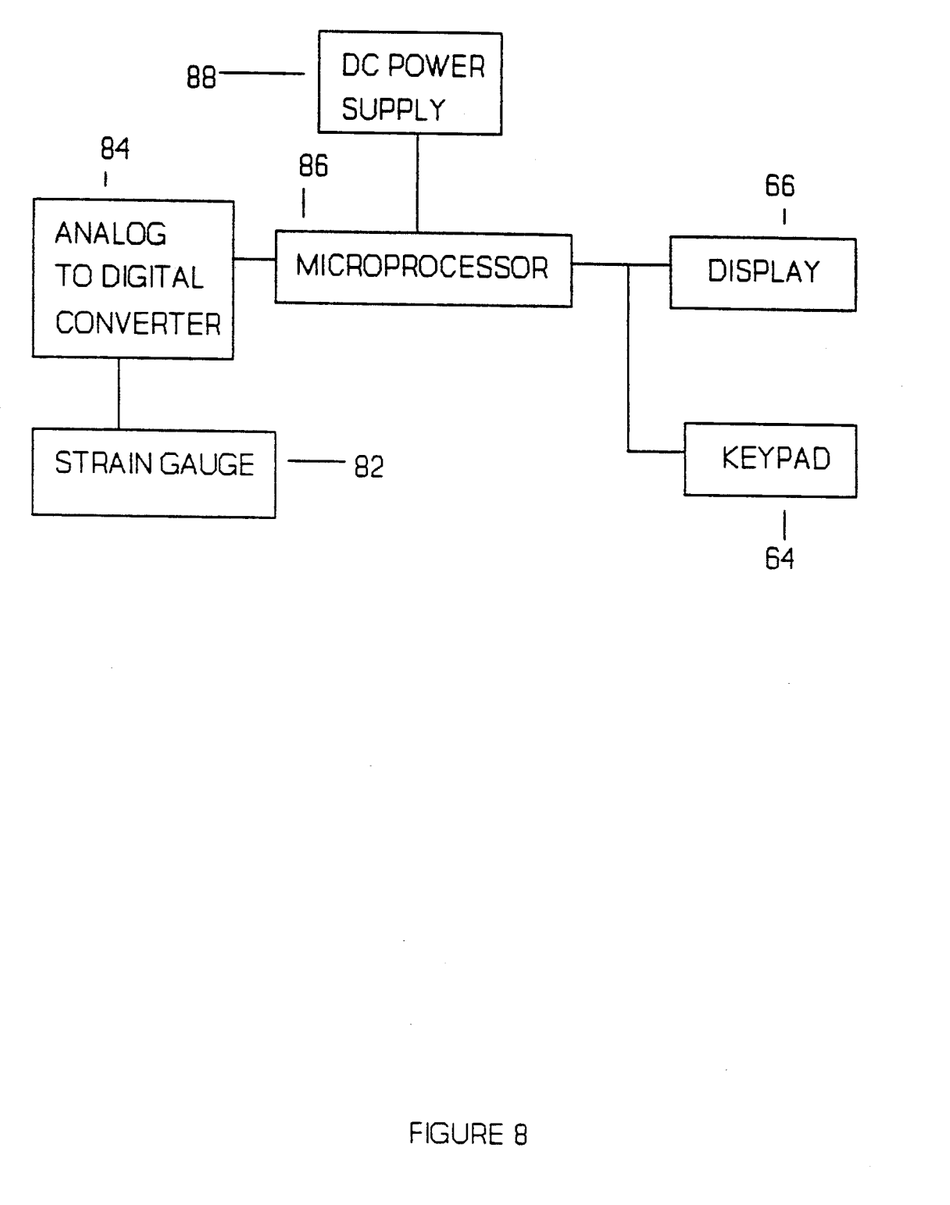
FIG. 8 is a diagram of the major electronic components.

FIG. 8 provides a diagram of the electronics that are located inside electronics box 62. Strain gauges 82 are mounted to the strain gauge rod 60 in such a manner as to measure strain on the strain gauge rod 60. The strain gauges 82 are electrically connected to an analog-to-digital converter 84. The analog-to-digital convertor 84 is electrically connected to a microprocessor 86. The microprocessor 86 is electrically connected to both the keypad 64 and the display 66. All the electronic components are powered by a DC power supply 88.

Figure 9:
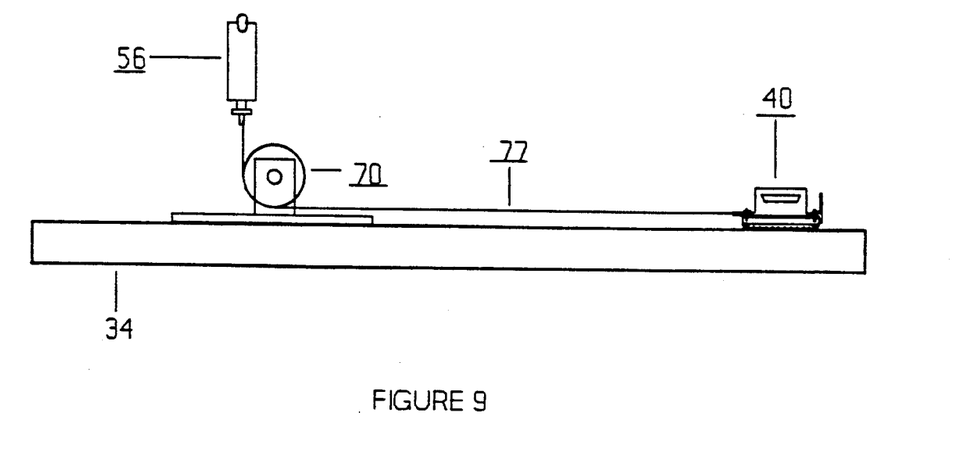
FIG. 9 provides a view of the device in just prior to use.

FIG. 9 shows the invention with all components attached just prior to use. The dragging cable 78 is attached to the dragging device 40 by connecting dragging cable clip 80 to dragging attachment eyebolt 54. The dragging cable 78 passes through the pulley 72 located on the foot held pulley device 70. The other end of dragging cable 78 is attached to the pulling/measuring device 56 by attaching dragging cable eye 81 to the pulling clip 58.

Figure 10:
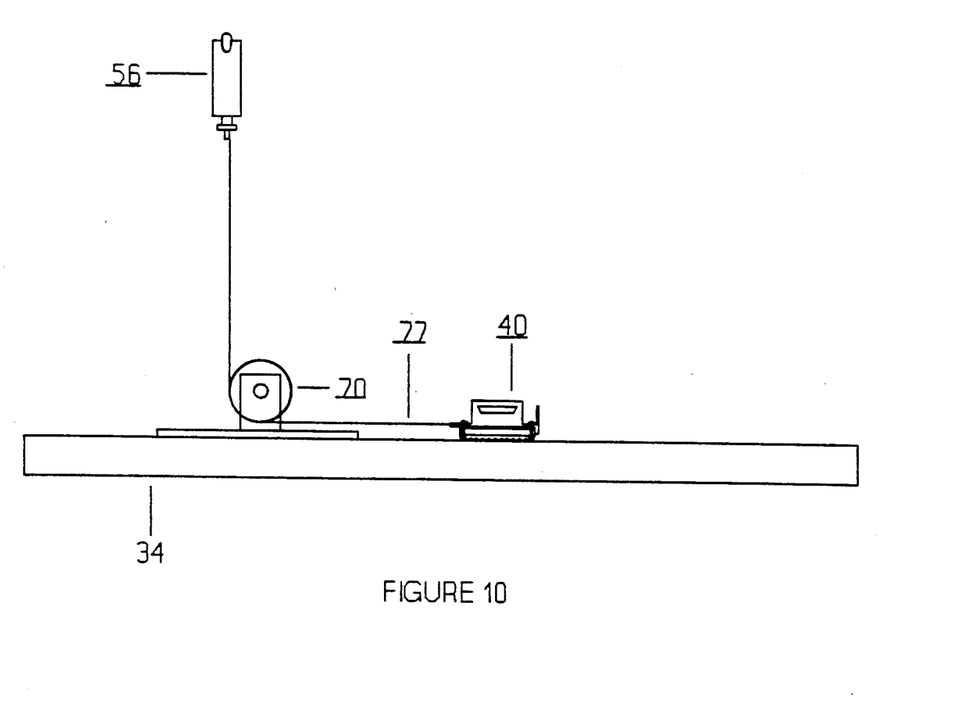
FIG. 10 provides a view of the device just after use.

FIG. 10 shows the invention with all components attached just after use.

Figure 11:
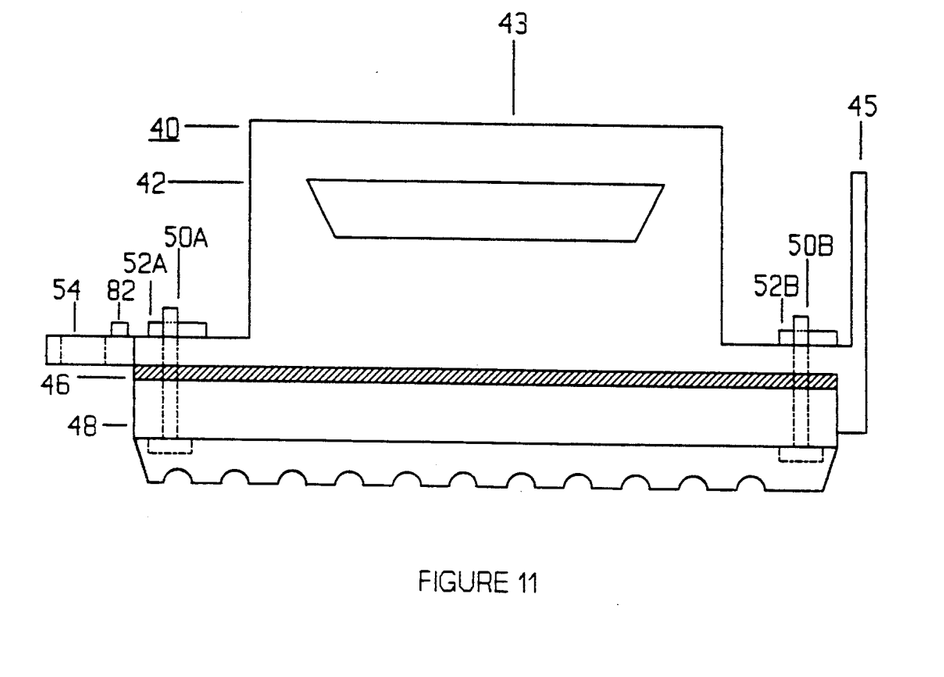
FIG. 11 provides a side view of the dragging device with a strain measuring device mounted on the dragging device.

FIG. 11 shows the dragging device 40 with strain gauge 82 attached.

Figure 12:
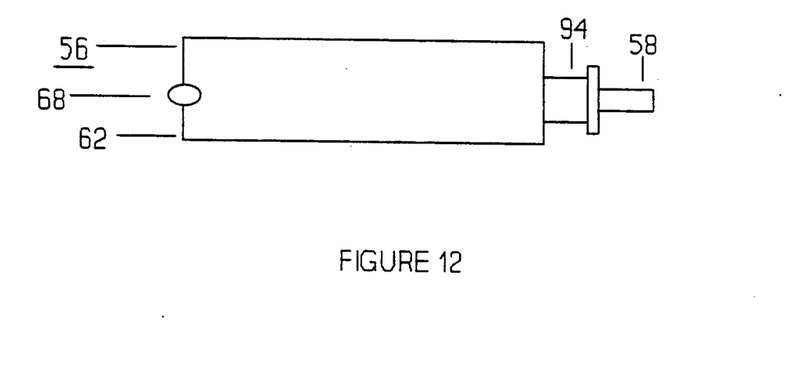
FIG. 12 provides a side view of the pulling/measuring device with the strain gauge rod replaced by a rod.

FIG. 12 shows a side view of the pulling/measuring device 56 with rod 92 that does not have strain gauges 82 attached.

Figure 13:
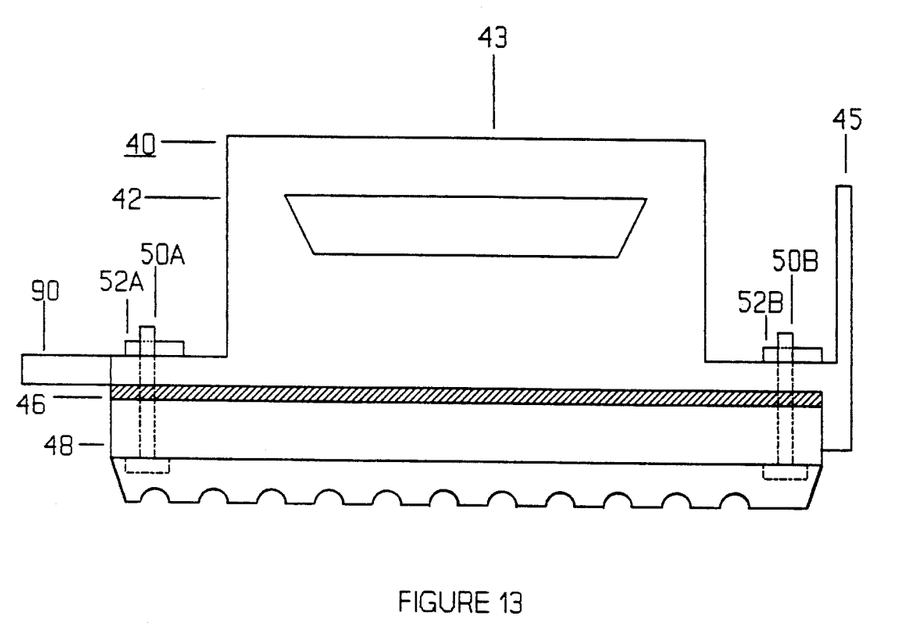
FIG. 13 provides a side view of the dragging device with an angle measuring device mounted on the dragging device.

FIG. 13 shows a side view of the dragging device 40 with an angle measuring device 90.

Figure 14:
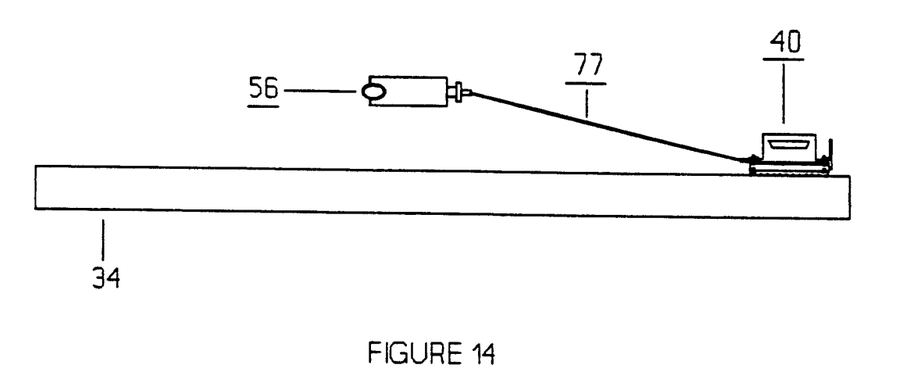
FIG. 14 shows the invention with all components attached just prior to use when utilizing the angle measuring device.

FIG. 14 shows the invention just prior to use when the angle measuring device 90 is used.

Figure 15:
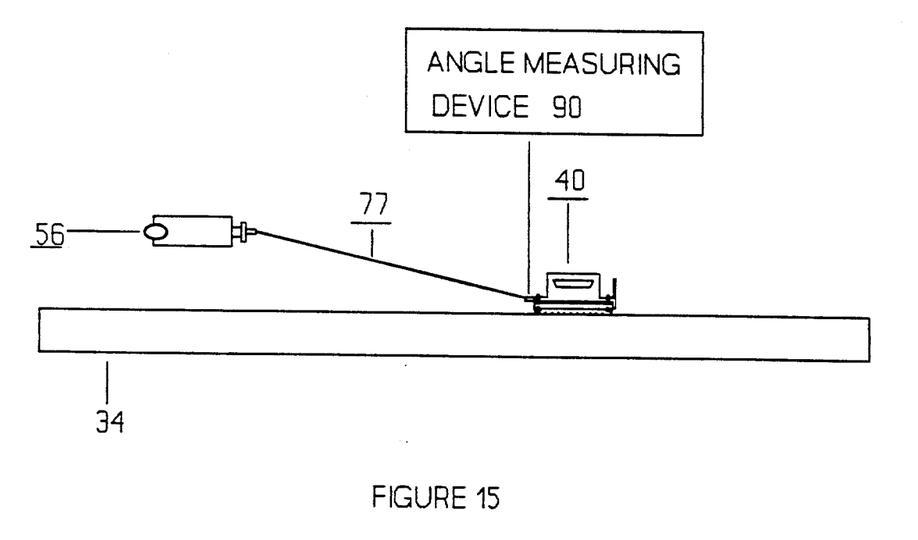
FIG. 15 shows the invention with all components attached just after use when utilizing the angle measuring device.

FIG. 15 shows the invention just after use when the angle measuring device 90 is used.

OPERATION OF INVENTION

The first step in using the invention is to select a replaceable friction pad 48 that is made out of the material for which the drag factor is to be determined. The free floating cushion pad 46 is placed on top of the replaceable friction pad 48 and the weight 42 is placed on top of the free floating cushion pad 46. The holes in the replaceable friction pad 48 and the free floating cushion pad 46 and the weight 42 are aligned. The friction pad retention pins 50A&B are inserted through the aligned holes and secured with the cotter pins 52A&B. Changing the material to be tested is quick and easy. First, the replaceable friction pad 48 is removed by removing the cotter pins 52A&B which allows for the removal of the friction pad retention pins 50A&B. The replaceable friction pad 48 is then replaced with a replaceable friction pad 48 made out of the new material to be tested and the friction pad retention pins 50A&B and the cotter pins 52A&B reinstalled. The dragging device 40 may be easily carried to the test site by using the carrying handle 43.

The pulling/measuring device 56 is then turned on by pressing the on/off switch on the keypad 64. The DC power supply 88 then provides power to all the electronic components. The word "ENGLISH" appears on the display 66. If the user desires the readings to be in metric units the user can press the "NEXT" button on the keypad 64. The display 66 will then show the word "METRIC". The user may toggle back and forth between english and metric units by pressing the next "NEXT" button on the keypad 64. When the desired units have been selected the user presses the "ENTER" button on the keypad 64 and the word "WEIGH" then appears in the display 66. The pulling/measuring device 56 is then attached to the dragging device 40 by attaching the pulling clip 58 to the dragging attachment eyebolt 54. The dragging device 40 is then stood upright so that the dragging device 40 rests on the butt plate 45. Holding handgrip 68, the user then lifts the dragging device 40 with a smooth motion. The strain placed on the strain gauge rod 60 is sensed by the strain gauges 82 that are mounted on the strain gauge rod 60. The information is transmitted electronically to the microprocessor 86. The microprocessor 86 uses this strain information to calculate the weight of the dragging device 40. The weight of the dragging device 40 is then stored in the microprocessor 86 memory and is also shown on the display 66. The user then sets the dragging device 40 down. The user then presses the "ENTER" button on the keypad 64. The message "PULL TEST" will then appear on the display 66. Pulling clip 58 is then disengaged from the dragging attachment eyebolt 54. The components of the invention are then assembled as shown in FIG. 9. The dragging device 40 is placed on the test surface with the replaceable friction pad 48 resting on the test surface. The dragging cable 78 is then attached to the dragging device 40 by engaging the dragging cable clip 80 with the dragging attachment eyebolt 54. The foot held pulling device 70 is placed on the ground in line with the dragging device 40 and at a distance from the dragging device 40 that will use up most of the slack in the dragging cable 78. The dragging cable 78 is then passed through the pulley 72 on the foot held pulley device 70. The pulling/measuring device 56 is then attached to the dragging cable 78 by engaging the pulling clip 58 with the dragging cable eye 81. The invention is now ready for the actual test.

In preparation for using the device, the user stands on the footrest 76, bends down and grasps the handgrip 68. In a smooth and continuous motion, the user stands up. This pulls the dragging device 40 along the test surface. The pulley supports 74A&B hold the pulley 72 at the proper height to assure that the pull is made parallel to the test surface 34. This is to prevent the dragging device 40 from being pulled up off the test surface or being pulled down into the test surface. Either of these conditions would result in measurement error. Error caused by drag sled hop is minimized by the action of the free floating cushion pad 46. The free floating cushion pad 46 acts as a shock absorber to minimize drag sled hop.

As the dragging device 40 is pulled along the test surface 34, the static and dynamic forces caused by the friction between the test surface 34 and the replaceable friction pad 48 are transmitted via the cable assembly 77 to the strain gauge rod 60. This creates a strain on the strain gauge rod 60 which is measured by the strain gauges 82 that are mounted on the strain gauge rod 60.

This strain information is transmitted electronically to the analog-to-digital convertor 84 which transforms the incoming analog information into digital signals. The digital signals are then transmitted electronically to the microprocessor 86. When the pull is complete the user presses the "ENTER" key on the keypad 64. The display 66, will read "DYN", if the static drag factor is desired the "NEXT" key is pressed again and the display 66 will show "STA". When the desired mode is showing on the display 66, the "ENTER" key is pressed on the keypad. The microprocessor 86 then uses the strain information and the previously measured weight of the dragging device 40 to calculate the desired slope compensated drag factor. The selected slope compensated drag factor will then be shown on the display 66. These drag factors may be used directly in traditional accident reconstruction relationships, without the need for a correction grade drag factor. If there was a problem with the pull such as the pull was not smooth or continuous or if the dragging device hops, the strain information will reflect this. The microprocessor 86 will then cause the display 66 to indicate that the test was not valid and should be run again.

CONCLUSION, RAMIFICATIONS, AND SCOPE OF INVENTION

Thus, the reader will see that the invention will provide a device that will quickly and easily provide measurement of slope compensated static and dynamic drag factors through assuring proper alignment, reducing hop, and by informing the user if there was a problem with the test such as an erratic pull. In addition, the invention provides the ability to easily and rapidly test a number of different materials. Also, the invention is truly portable.

While the above description contains many specificities, these should not be construed as limitations on the scope of the invention, but rather as an exemplification of one preferred embodiment thereof. Many other variations are possible. For example:

(a) the free floating cushion pad 46 may be permanently attached to either the weight 42 or the replaceable friction pad 48;

(b) some of the device electronics may be built into the dragging device 40;

(c) the butt plate 45 may be eliminated;

(d) as shown in FIGS. 11 and 12, instead of measuring the strain on the strain gauge rod 60 the strain may be measured on the dragging device 40 by replacing strain gauge rod 60 with a rod 92 that does not have strain gauge 82 mounted on it and mounting strain gauge 82 on the dragging device 40;

(e) drag factors for relatively high speeds, such as over 30 MPH (50 KPH), may be estimated by applying predetermined reputable test results which have established an average adjustment factor;

(f) as shown in FIGS. 13, 14 and 15 the dragging cable assembly 77 could be attached to the dragging device 40. Utilizing an angle measuring device 90, an average pulling angle could be established for a non-parallel pull. The electronics could then make the appropriate calculation adjustments to render the same results as would have been derived from a parallel pull. This would eliminate the need for a foot held pulley device 70.

Accordingly, the scope of the invention should be determined not by the embodiment(s) illustrated, but by the appended claims and their equivalents.

We claim:

1. A portable testing device for measuring static and dynamic drag factors, comprising:

(a) a sheet of test material, (b) a sheet of shock absorbing material of the same approximate length and width as said sheet of test material, (c) a weight made of rigid material with a flat bottom surface of the same approximate width and longer than said sheet of test material and said weight formed with a vertical butt plate on one end said butt plate extending down a distance greater than the thickness of said sheet of shock absorbing material but less than the sum of the thicknesses of said sheet of shock absorbing material and said sheet of test material and a carrying handle integrally molded into said weight, (d) said sheet of shock absorbing material placed on top of said sheet of test material and said weight placed on top of said sheet of shock absorbing material with said butt plate in contact with the sides of said sheet of shock absorbing material and said sheet of test material, (e) an attachment means that will allow said sheet of test material and said sheet of shock absorbing material and said weight to be held together and later taken apart, (f) a container with a keypad and a display device which are accessible from outside said container, (g) a handgrip firmly attached to said container, (h) a rod of rigid material firmly attached to said container and that extends outside of said container, (i) means of measuring the strain experienced by said rod, (j) means of transmitting the strain measured on said rod to a microprocessor, (k) means for said microprocessor to calculate and store weight using the strain information measured on said rod, (l) means for said microprocessor to calculate and store static and dynamic drag factors using the calculated weight and the strain measured on said rod, (m) means for said microprocessor to accept instructions from said keypad and means for said microprocessor to show information including static drag factor and dynamic drag factor on said display, (n) means for said microprocessor to determine if the strain measured on said rod was within acceptable parameters, (o) a cable with means to attach one end of said cable to the end of said weight opposite said butt plate and means to attach the other end of said cable to the end of said rod that extends out of said container, (p) a rigid plate of sufficient size that a person could stand on it, (q) a cable redirection device capable of redirecting said cable from parallel to the test surface to vertical and a means of attaching said cable redirection device to said rigid plate so that said cable will remain at approximately the same height above the test surface between said cable redirection device and said weight.

2. The portable testing device for measuring static and dynamic drag factors of claim 1 wherein said cable redirection device is a pulley.

3. The portable testing device for measuring static and dynamic drag factors of claim 1 wherein said sheet of shock absorbing material is permanently affixed to said weight.

4. The portable testing device for measuring static and dynamic drag factors of claim 1 wherein said sheet of shock absorbing material is permanently affixed to said sheet of test material.

5. A portable testing device for measuring static and dynamic drag factors, comprising:
   (a) a sheet of test material,
   (b) a sheet of shock absorbing material of the same approximate length and width as said sheet of test material,
   (c) a weight made of rigid material with a flat bottom surface of the same approximate width and longer than said sheet of test material and said weight formed with a vertical butt plate on one end, said butt plate extending down a distance greater than the thickness of said sheet of shock absorbing material but less than the sum of the thicknesses of said sheet of shock absorbing material and said sheet of test material and a carrying handle integrally molded into said weight,
   (d) means to measure an angle of pull,
   (e) said sheet of shock absorbing material placed on top of said sheet of test material and said weight placed on top of said sheet of shock absorbing material with said butt plate in contact with the sides of said sheet of shock absorbing material and said sheet of test material,
   (f) an attachment means that will allow said sheet of test material and said sheet of shock absorbing material and said weight to be held together and later taken apart,
   (g) a container with a keypad and a display device which are accessible from outside said container,
   (h) a handgrip firmly attached to said container,
   (i) a rod of rigid material firmly attached to said container and that extends outside of said container,
   (j) a cable with means to attach one end of said cable to weight and means to attach the other end of said cable to the end of said rod that extends out of said container the means to measure an angle of pull being used to measure the angle of pull on the cable,
   (k) means of measuring the strain experienced by said rod,
   (l) means of transmitting the strain measured on said rod and the angle of pull measured on said cable by said angle measuring device to a microprocessor,
   (m) means for said microprocessor to calculate and store weight using the strain information measured on said rod,
   (o) means for said microprocessor to calculate and store static and dynamic drag factors using the calculated weight and the strain measured on said rod and the measured angle of pull on said cable,
   (p) means for said microprocessor to accept instructions from said keypad and means for said microprocessor to show information including static drag factor and dynamic drag factor on said display,
   (q) means for said microprocessor to determine based on the strain measured on said rod and the measured angle of pull on said cable if the test was within acceptable parameters,
   (r) a rigid plate of sufficient size that a person could stand on it,
   (s) a cable redirection device capable of redirecting said cable from parallel to the test surface to vertical and a means of attaching said cable redirection device to said rigid plate so that said cable will remain at approximately the same height above the test surface between said cable redirection device and said weight.

6. The portable testing device for measuring static and dynamic drag factors of claim 5 wherein said cable redirection device is a pulley.

7. The portable testing device for measuring static and dynamic drag factors of claim 5 wherein said sheet of shock absorbing material is permanent a to said weight.

8. The portable testing device for measuring static and dynamic drag factors of claim 5 wherein said sheet of shock absorbing material is permanently affixed to said sheet of test material.

9. A portable testing device for measuring static and dynamic drag factors, comprising:
   (a) a sheet of test material,
   (b) a sheet of shock absorbing material of the same approximate length and width as said sheet of test material,
   (c) a weight made of rigid material with a flat bottom surface of the same approximate width and longer than said sheet of test material and said weight formed with a vertical butt plate on one end said butt plate extending down a distance greater than the thickness of said sheet of shock absorbing material but less than the sum of the thicknesses of said sheet of shock absorbing material and said sheet of test material and a carrying handle integrally molded into said weight,
   (d) said sheet of shock absorbing material placed on top of said sheet of test material and said weight placed on top of said sheet of shock absorbing material with said butt plate in contact with the sides of said sheet of shock absorbing material and said sheet of test material,
   (e) an attachment means that will allow said sheet of test material and said sheet of shock absorbing material and said weight to be held together and later taken apart,
   (f) a container with a keypad and a display device which are accessible from outside said container,
   (g) a handgrip firmly attached to said container,
   (h) a rod of rigid material firmly attached to said container and that extends outside of said container,
   (i) means of measuring the strain experienced by said weight,
   (j) means of transmitting the strain measured on said weight to a microprocessor,
   (k) means for said microprocessor to calculate and store weight using the strain information measured, on said weight,
   (l) means for said microprocessor to calculate and store static and dynamic drag factors using the calculated weight and the strain measured on said weight,
   (m) means for said microprocessor to accept instructions from said keypad and means for said microprocessor to show information including static drag factor and dynamic drag factor on said display, (n) means for said microprocessor to determine if the strain measured on said weight was within acceptable parameters, (o) a cable with means to attach one end of said cable to the end of said weight opposite said butt plate and means to attach the other end of said cable to the end of said rod that extends out of said container, (p) a rigid plate of sufficient size that a person could stand on it, (q) a cable redirection device capable of redirecting said cable from parallel to the test surface to vertical and a means of attaching said cable redirection device to said rigid plate so that said cable will remain at approximately the same height above the test surface between said cable redirection device and said weight.

10. The portable testing device for measuring static and dynamic drag factors of claim 9 wherein said cable redirection device is a pulley.

11. The portable testing device for measuring static and dynamic drag factors of claim 9 wherein said sheet of shock absorbing material is permanently affixed to said weight.

12. The portable testing device for measuring static and dynamic drag factors of claim 9 wherein said sheet of shock absorbing material is permanently affixed to said sheet of test material.

* * * * *